United States Patent [19]

Pellar

[11] Patent Number: 5,753,232

[45] Date of Patent: May 19, 1998

[54] INGESTIBLE SYRUP FOR SOFTENING THE STOOL AND IMPROVING REGULARITY OF ELIMINATION

[76] Inventor: Marshall Pellar, 12991 Via Esperia, Del Mar, Calif. 92014-3722

[21] Appl. No.: 695,917

[22] Filed: Aug. 12, 1996

[51] Int. Cl.$^6$ ............................................. A01N 65/00
[52] U.S. Cl. ............................................. 424/195.1
[58] Field of Search ............................................. 424/195.1

[56] References Cited

U.S. PATENT DOCUMENTS

| | | | |
|---|---|---|---|
| 4,231,263 | 11/1980 | Powell et al. | 424/195.1 |
| 5,223,298 | 6/1993 | Wullscleger et al. | 426/549 |

Primary Examiner—Leon B. Lankford, Jr.

[57] ABSTRACT

An ingestible composition for reducing constipation, softening the stool and promoting elimination regularity which includes from about 90 to 99 vol % prune concentrate and from about 10 to 1 vol % psyllium powder. The mixture is a stable, pourable syrup that may be easily consumed. Prune concentrate is prepared, basically, by boiling ripe prunes until soft, pitting the prunes and pulverizing them until a mixture of finely divided prune fiber in prune juice results. The psyllium powder may be mixed immediately before ingestion, or may be mixed in advance of use. Where users may wish to vary the proportion of psyllium powder used within the 1 to 10 vol % range, a container having two compartments, a large compartment containing prune concentrate and a small compartment containing psyllium powder is particularly convenient.

9 Claims, 1 Drawing Sheet

INGESTIBLE SYRUP FOR SOFTENING THE STOOL AND IMPROVING REGULARITY OF ELIMINATION

BACKGROUND OF THE INVENTION

This invention relates to a composition and method of making the composition which when ingested will improve regularity of elimination, soften the stool and provide other advantages resulting from the high fiber characteristics of the composition.

A variety of laxative compositions have been developed over the years, having both chemical and natural ingredients for correcting constipation. These are intended to be used only when a problem occurs. Many are harsh and cannot be used regularly.

In order to improve regularity of elimination, high fiber fruits and grains are often eaten fairly regularly, with mixed results.

High-fiber products made up of finely ground psyllium husks, bran, semi-synthetic fibers such as methyl cellulose or calcium polycarbophil are sometimes ingested in the form of beverages as described by Langer in U.S. Pat. No. 5,254,357 or as ready to eat breakfast cereals as described by Wullschleger et al. in U.S. Pat. No. 5,227,248. These products are believed to reduce the incidence of various diseases such as diabetes, coronary heart disease, colorectal cancer and disorders such as constipation, hemorrhoids and diverticular problems.

Psyllium powder alone, dispersed in water is used as a bulk laxative. However, the powder is often difficult to disperse in water, will gel if not consumed immediately and has been known to plug the esophagal. Such powders generally are mixed with significant quantities of sugars and with dispersing agents of the sort described by Powell et al. in U.S. Pat. No. 4,321,263. These powders must be mixed with water immediately before use due to the gelling problem.

As laxatives, these various prior compositions are generally only taken when a problem of constipation or the like exists.

Therefore, there is a continuing need for improved fiber compositions that can be mixed into a stable syrup-like liquid for convenient measuring and ingestion, that may be taken regularly if desired without significant detrimental side effects, that will maintain a soft stool and promote regular elimination, in addition the other known or suspected benefits of increased fiber consumption.

SUMMARY OF THE INVENTION

The above-noted problems, and others by a composition consisting essentially of a mixture of from about 90 to 99 vol % prune concentrate and from about 1 to 10 vol % psyllium powder.

The mixture is prepared, basically, by boiling a quantity of prunes for an appropriate period, pitting the prunes, pulverizing the prunes to form a dispersion of prune particles in prune juice, then mixing finely divided psyllium powder into the prune juice to form a mixture having from about 1 to 10 vol % psyllium.

The mixture has been found to provide an optimum combination of a hydrocolloid and humectant for moisture retention to promote formation of a soft stool, soluble and insoluble fibers for bulk and unfermented natural sugars to encourage beneficial bacterial growth for digestive improvement.

The quantity ingested may vary depending on the problem being treated. A typical dose would be from about one to two level teaspoons, with up to about three doses per day. Since the mixture is formed from all natural ingredients with no significant side effects, there is little problems with taking higher greater amounts, although there is little, if any, benefit in taking more than ten level teaspoons each day.

During testing of various compositions, I have found that in order to assure regularity and formation of a soft stool, the composition requires a hydrocolloid and humectant for moisture retention, soluble and insoluble fibers for bulk and unfermented sugars to encourage bacterial growth for digestive purposes. An analysis of prune concentrate shows 14% sorbitol (a humectant), 3.47% various hydrocolloids, such as gums, gels, pectins and 0.79% unfermented sugars. I found that additional hydrocolloids greatly enhance the natural laxative characteristics of prune concentrate without need for harsh habit forming chemicals. Small amounts, preferably 1 to 10% of finely ground psyllium, which is about 38% hydrocolloids, was found to meet this need.

It is, therefore, an object of this invention to provide a beneficial composition which, when ingested will soften the stool. Another object is to provide a composition containing an optimum proportion of hydrocolloids and humectants for moisture retention to promote soft stool formation. A further object is to provide a composition containing an optimum proportion of soluble and insoluble fibers for stool bulk. Yet another object is to provide a composition containing an optimum proportion of natural sugars to encourage beneficial bacterial growth for improved digestion. Still another object is to provide a composition which has a stable, pourable, syrup-like consistency for ease of measuring and ingestion. A still further object is to provide a composition that can be incorporated in cereals, bakery products, confections, and the like.

BRIEF DESCRIPTION OF THE DRAWING

Details of the invention, and of preferred embodiments thereof, will be further understood upon reference to the drawing, wherein.

DETAILED DESCRIPTION OF PREFERRED EMBODIMENTS

Figure 1:
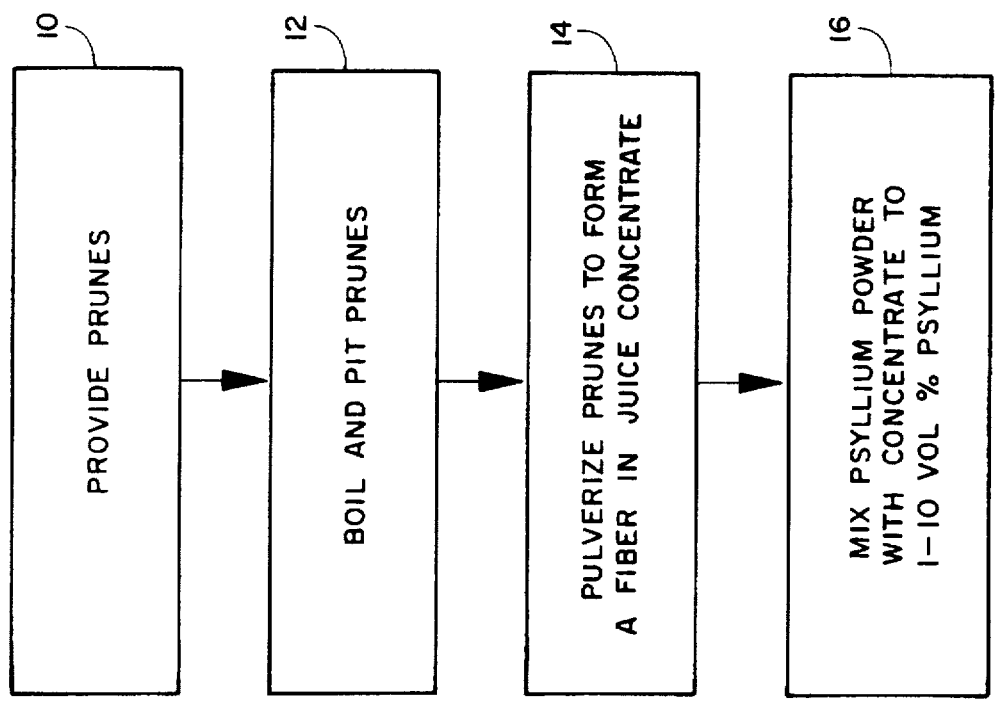
FIG. 1 is a flow diagram of the method of this invention.

The method of preparing the composition of this invention is outlined in the flow diagram of FIG. 1. This method begins with selecting a quantity of prunes as indicated in Step 10. Any variety of prunes may be used. Best result are obtained with the well known D'Agen prunes, a French variety often grown in California. variety.

The prunes are then boiled in water, as indicated in Step 12 for from about one to six hours at sea level. At higher elevations, the boiling period would be extended in proportion to the decrease in boiling temperature for water at the elevation. The prunes are then pitted.

The prunes are then pulverized to form a mixture of prune particles in prune juice as indicated in Step 14. The prune solids may be pulverized to any suitable particle size. For optimum results, particles having diameters of from about 20 μm to 2 mm are preferred. While any suitable pulverizer may be used, a hammer mill type machine, such as the Fitzmill from the Fitzmill company is preferred.

The resulting prune concentrate is then mixed, as indicated in Step 16, with the desired amount of finely powdered psyllium in any suitable mixer. The mixture may be formed just before it is to be ingested or may be prepackaged as a stable, pourable, syrup-like liquid which is easily poured into a standard table spoon or small cup with little chance of spilling.

Where the prune concentrate and psyllium powder are mixed just before the mixture is ingested, any desired proportions could be used, although no benefits are achieved with a mixture containing more than about 10 vol % psyllium. In general, a smaller amount of psyllium powder, about 1 vol %, provides maximum benefits.

Figure 2:
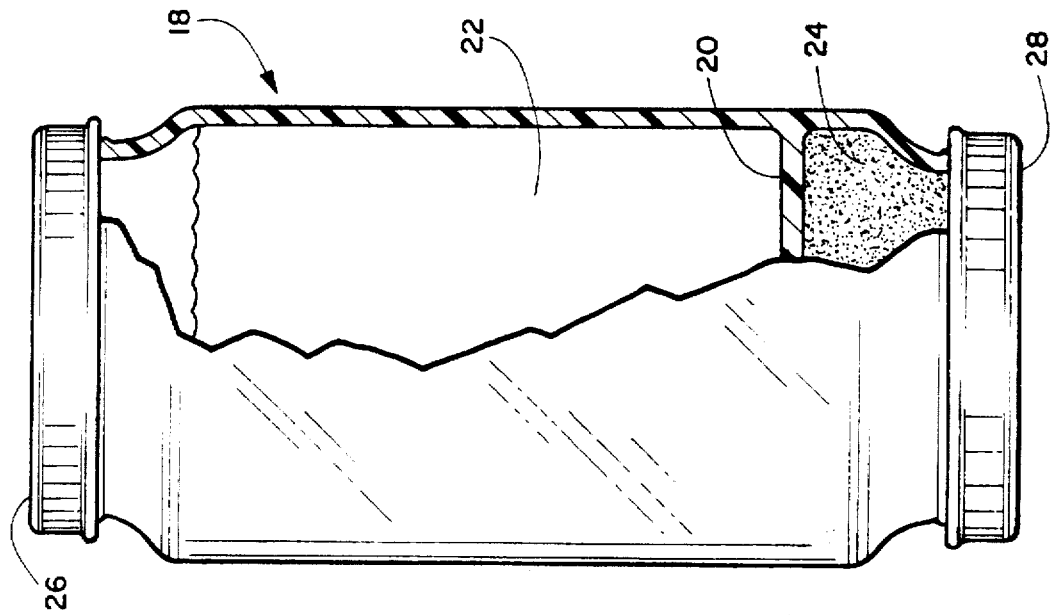
FIG. 2 is a front elevation view, partly cut-away, of a dual container for the product.

To allow a user to vary the amount of psyllium powder within the preferred range of 1 to 10 vol %, a two compartment container 18 as seen in FIG. 2 may be used. Container 18 is preferably generally cylindrical in shape, with an internal wall 20 dividing the container into two compartments, a prune concentrate compartment 22 and a psyllium compartment 24. Preferably, the ratio of compartment 22 to compartment 24 is approximately 10 to 1, so that mixing the contents of the entire container will produce a mixture in the preferred range.

Wide lids 26 and 28 close openings in compartment 22 and 24, respectively. The prune concentrate in compartment 22 may be poured or spooned into a mixing vessel, that compartment closed by replacing lid 26, the container inverted and lid 28 removed to allow the selected quantity of psyllium powder to be removed and mixed in the vessel with the prune concentrate.

The composition was tested with a group of people who were experiencing problems with constipation, had stool and irregular elimination. The group was divided into several sets, one ingesting only prune concentrate, another only psyllium powder mixed with water, and others using a mixture of prune concentrate with 1, 10 and 50 vol % psyllium powder.

The compositions containing more than 10 vol % psyllium were found to gel rather quickly after mixing, to have a gritty feel and to be unusable in a packaged syrup form do to the gelling. Therefore, those using the higher proportions of psyllium had to very promptly mix the ingredients and ingest the mixture. Those using the lower proportion of psyllium were able to easily measure and consume the resulting syrup, which could be stored for several days without gelling.

Each of the groups experienced improvement in their condition. The most effective softening of the stool and improvement in regularity of elimination occurred with the group using prune concentrate with 1 and 10 vol % psyllium. The groups using only psyllium or only prune concentrates still experienced problems with hard stools, elimination and regularity. The groups using 1 and 10 vol % psyllium in prune concentrate had better results than those using either psyllium in prune concentrate alone. Apparently, there is a synergistic effect from the combination.

Thus, it became apparent for optimum stool softening and bowel regularity effectiveness, a mixture of from about 1 to 10 vol % psyllium mixed into prune concentrate should be used.

While certain specific relationships, materials and other parameters have been detailed in the above description of preferred embodiments, those can be varied, where suitable, with similar results. Other applications, variations and ramifications of the present invention will occur to those skilled in the art upon reading the present disclosure. Those are intended to be included within the scope of this invention as defined in the appended claims.

I claim:

1. An ingestible syrup for softening the stool and improving regularity of elimination which consists essentially of:

from about 90 to 99 vol % prune concentrate; and from about 1 to 10 vol % psyllium powder dispersed therein to form a syrup.

2. The syrup according to claim 1 wherein said prune concentrate is in the form of a mixture of pulverized pitted prune fiber in prune juice resulting from the pulverization.

3. A method of making an ingestible syrup for softening the stool and improving regularity of elimination which comprises:

providing a quantity of essentially ripe prunes;

boiling said prunes until said prunes have a generally soft consistency;

pitting said prunes;

pulverizing said prunes to produce a mixture of juice and finely divided prune fiber;

providing a quantity of psyllium powder adding from about 1 to 10 parts by weight of said psyllium powder to from about 90 to 99 parts by weight of said prune concentrate;

mixing the resulting composition to form a stable, easily pourable, syrup-like composition.

4. The method according to claim 3 wherein said prunes are boiled for from about 1 to 6 hours.

5. The method according to claim 3 wherein said prunes after pitting are pulverized by passing said pitted prunes through a hammer mill pulverizer.

6. The method according to claim 3 wherein said mixture contains about 1 vol % psyllium, the balance consisting essentially of prune concentrate.

7. A method of softening the stool and improving regularity of elimination which comprises;

providing a syrup-like mixture consisting essentially of from about 90 to 99 vol % prune concentrate and from about 1 to 10 vol % psyllium powder dispersed therein; and swallowing from about 1 to 6 teaspoons of said mixture each day.

8. The method according to claim 7 wherein said prune concentrate is formed by pulverizing pitted prunes to form a mixture of finely divided prune fiber in prune juice resulting from said pulverization.

9. A package containing prune concentrate and psyllium powder for convenient mixing and consumption which comprises:

a generally cylindrical container having open ends;

lids for removably closing said ends;

a transverse wall across said container dividing said container into first and second compartments;

said first compartment containing psyllium powder and having a volume of from about 1 to 10 vol % of the volume of said second compartment, said second compartment containing prune concentrate;

whereby said prune concentrate and said psyllium powder may be conveniently measured and sequentially mixed into a mixture of prune concentrate containing from about 1 to 10 vol % psyllium powder.

* * * * *